United States Patent
Giovanniello

(10) Patent No.: US 9,924,713 B2
(45) Date of Patent: *Mar. 27, 2018

(54) FORMULA AND PROCESS FOR CROSSLINKING ANTIMICROBIALS TO TEXTILES

(71) Applicant: Joseph Giovanniello, Haledon, NJ (US)

(72) Inventor: Joseph Giovanniello, Haledon, NJ (US)

(73) Assignee: Sanit Technologies LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/881,663

(22) Filed: Oct. 13, 2015

(65) Prior Publication Data

US 2016/0029620 A1 Feb. 4, 2016

Related U.S. Application Data

(60) Continuation of application No. 14/198,080, filed on Mar. 5, 2014, now Pat. No. 9,168,322, which is a division of application No. 13/661,579, filed on Oct. 26, 2012, now abandoned.

(51) Int. Cl.

| | |
|---|---|
| *A01N 25/02* | (2006.01) |
| *A01N 55/00* | (2006.01) |
| *A01N 33/12* | (2006.01) |
| *D06M 13/00* | (2006.01) |
| *A61L 2/232* | (2006.01) |
| *D06M 13/463* | (2006.01) |
| *D06M 13/513* | (2006.01) |
| *D06M 15/03* | (2006.01) |
| *D06M 16/00* | (2006.01) |

(52) U.S. Cl.
CPC ............. *A01N 25/02* (2013.01); *A01N 33/12* (2013.01); *A01N 55/00* (2013.01); *A61L 2/232* (2013.01); *D06M 13/00* (2013.01); *D06M 13/463* (2013.01); *D06M 13/513* (2013.01); *D06M 15/03* (2013.01); *D06M 16/00* (2013.01)

(58) Field of Classification Search
CPC ....................................... A01N 25/02
See application file for complete search history.

(56) References Cited

U.S. PATENT DOCUMENTS

| | | | | |
|---|---|---|---|---|
| 3,380,877 A | * | 4/1968 | Smucker | ................. C03C 25/34 156/180 |
| 2011/0293681 A1 | * | 12/2011 | Berlin | ..................... A61L 15/46 424/405 |

* cited by examiner

*Primary Examiner* — Adam C Milligan
*Assistant Examiner* — Sarah Alawadi
(74) *Attorney, Agent, or Firm* — Coats & Bennett PLLC

(57) ABSTRACT

This application is directed to methods of making a binder. In one embodiment, the method comprises mixing guar gum with water at a temperature greater than 145° F. A guar gum-water mixture is formed and then cooled to approximately 135-145° F. Ammonium sulfate and water are mixed with the guar gum-water mixture to form an ammonium sulfate-guar gum-water mixture. Urea is then mixed with the ammonium sulfate-guar gum-water mixture, forming a urea-ammonium sulfate-guar gum-water mixture. Water and methyl acryloid are added to the urea-ammonium sulfate-guar gum-water mixture to form the binder.

7 Claims, 3 Drawing Sheets

FORMULA AND PROCESS FOR CROSSLINKING ANTIMICROBIALS TO TEXTILES

CROSS REFERENCE TO RELATED APPLICATION

This is a continuation of U.S. patent application Ser. No. 14/198,080 filed Mar. 5, 2014, which is a divisional of U.S. patent application Ser. No. 13/661,579 filed Oct. 26, 2012. The disclosures of those patent applications are incorporated herein by reference.

BACKGROUND

Healthcare-associated infections "in hospitals are a significant cause or morbidity and mortality in the United States." R. Monina Klevens, et al., *Estimating Health Care-Associated Infections and Deaths in U.S. Hospitals*, 2002, Public Health Reports, 160-166 (March-April 2007). According to a study conducted by researchers at the CDC, Emory University School of Medicine, the Atlanta VA Medical Center, and the Atlanta VA Health Services Research and Development Center, during a one year period approximately 1.7 million people were infected by healthcare-associated infections in American hospitals, and slightly less than 100,000 of those infected died as a result. Id. (citing data from a study of the 2002 calendar year). These infections may be spread by, inter alia, hospital bedclothes and doctor clothing, such as scrubs.

One traditional approach to preventing the spread of healthcare-associated infections in hospitals is to treat fabrics used in hospitals with antimicrobial chemicals. Typically, these traditional treatments use silver salt antimicrobials to poison cell walls, DNA, and/or enzymes comprising the infectious agent.

These traditionally treated fabrics, however, suffer from numerous drawbacks. First, due to the process used to treat the substrates, the antimicrobial chemicals are applied in an uneven coating that wears off after a relatively low number of washes, thus greatly diminishing the effectiveness in preventing the spread of infectious agents. Second, because traditionally treated fabrics work by poisoning infectious agents, it is possible for the agents to develop resistance to the treatment. This results in the creation of a more dangerous infectious agent than the one originally targeted for destruction. Third, the silver salt antimicrobials used in traditional treatments require a substantial amount of contact time with an infectious agent to be effective in destroying the same. Fourth, traditional treatments may be easily neutralized by substances such as chlorine (which is commonly found in disinfectants such as bleach). This may result in the treatment losing its effectiveness to prevent infection from dangerous agents. Fifth, the silver salt antimicrobials have a tendency to leach into their surroundings. This may increase environmental risks, as well as health risks for the person coming in contact with the same. Further, traditional treatments are not always effective against the so-called "superbugs," i.e. resistant infectious agents such as, for example, Methicillin-resistant *Staphylococcus aureus* (MRSA).

There is a significant need for an improved treatment for fabric and other substrates used in the medical field to prevent the spread of healthcare-associated infections. There is further a need for such treatment to destroy infectious agents without risk of increasing resistance or creating resistant agents. There is also a need for treatment to destroy dangerous resistant infectious agents that would not be destroyed with traditional treatments.

SUMMARY

The present application is directed at a method of applying an antimicrobial to a fabric. An antimicrobial-binder mixture is applied to the fabric. The binder comprises guar gum. The antimicrobial is characterized as an organo silane quaternary amine capable of forming spiked structures.

The present application is further directed at a treated fabric for preventing the spread of infectious agents. Such fabric includes a fabric and an antimicrobial-binder mixture secured to that fabric. The antimicrobial-binder mixture contains a binder comprised of guar gum and an antimicrobial that includes an organo silane quaternary amine having spiked structures.

The present application is also directed to a binder solution. The binder solution is aqueous and comprised guar gum.

The present application is further directed to a method of making a binder. Guar gum with water at a temperature in excess of 145° F. to form a guar gum-water mixture. The guar gum-water mixture is cooled to approximately 135-145° F. Ammonium sulfate and water are added to the guar gum-water mixture to form an ammonium sulfate-guar gum-water mixture. The temperature of this mixture is less than or equal to 145° F. Urea is mixed to the ammonium sulfate-guar gum-water mixture to form a urea-ammonium sulfate-guar gum-water mixture. Water and methyl acryloid are then added to the urea-ammonium sulfate-guar gum-water mixture to form the binder.

DRAWINGS

DETAILED DESCRIPTION

Figure 1:
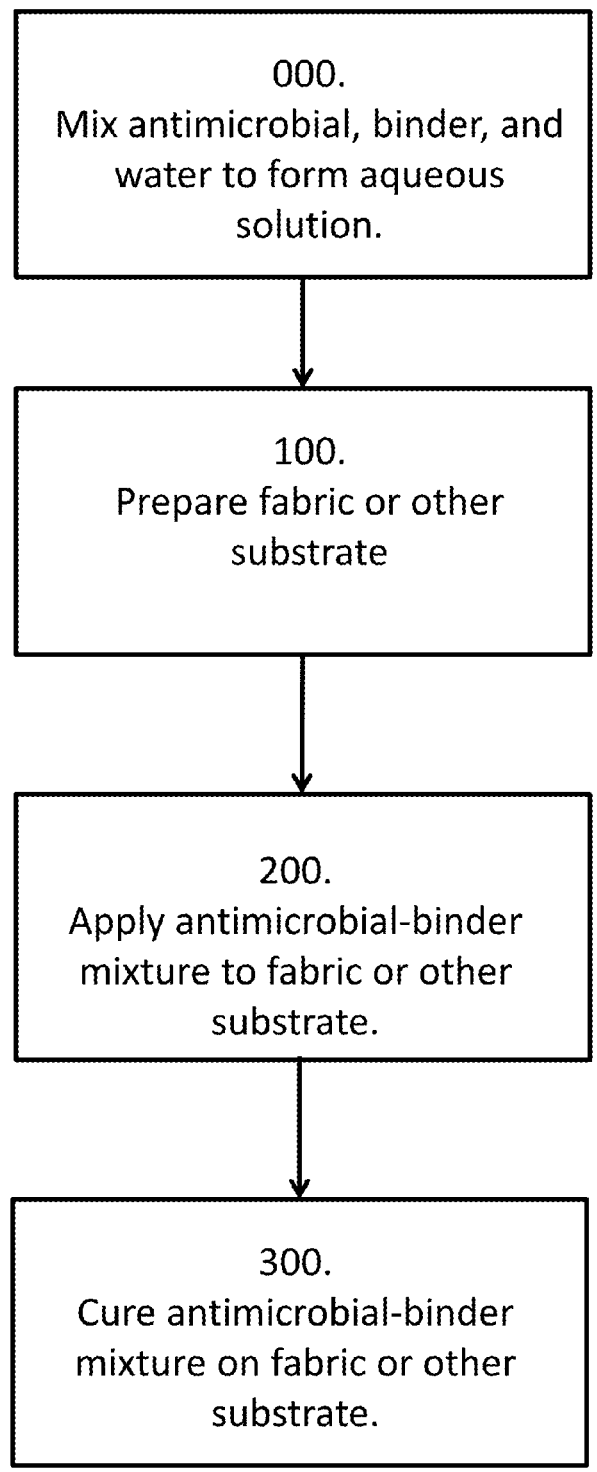
FIG. 1 depicts a flow chart of one embodiment of a method for applying an antimicrobial to a fabric.
Figure 2:
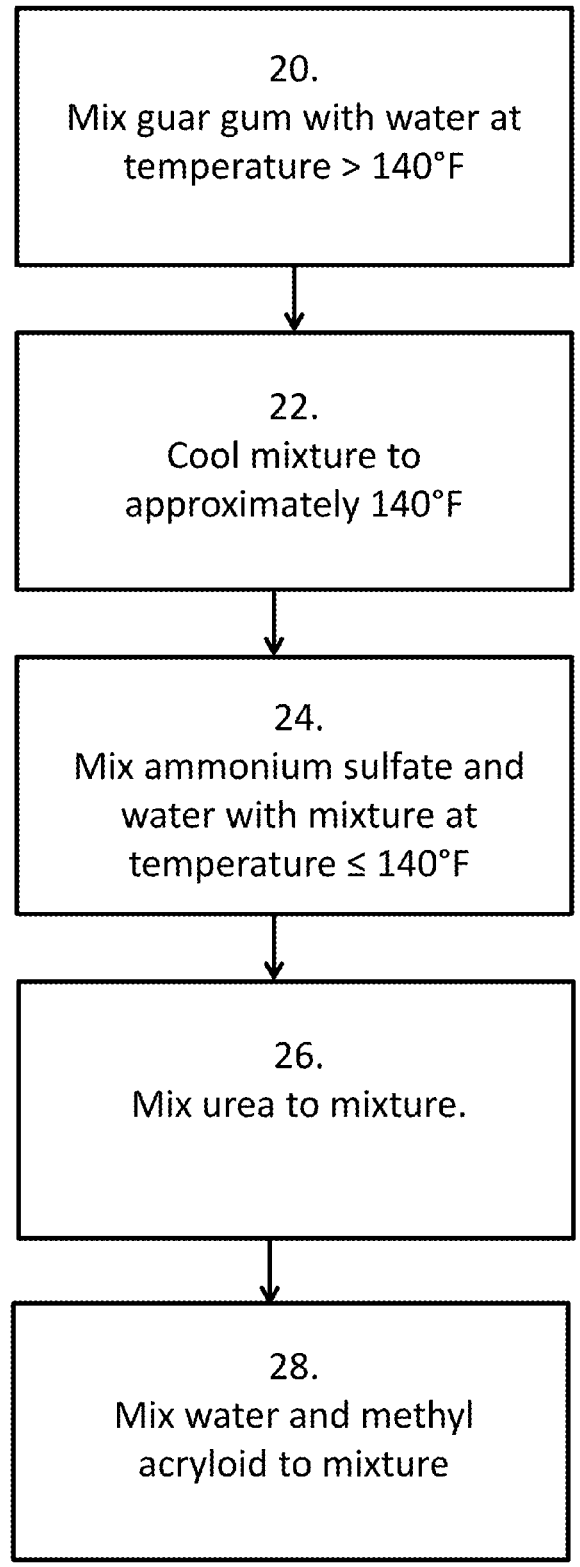
FIG. 2 depicts a flow chart of one embodiment of a method of making a binder.
Figure 3:
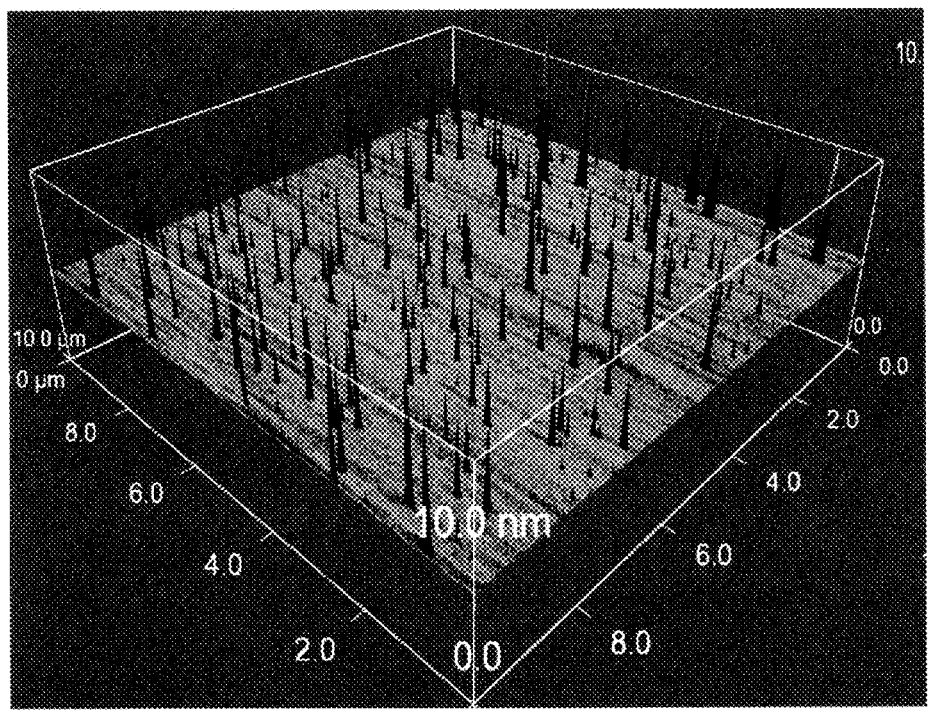
FIG. 3 depicts a diagram from a Scanning Tunneling Microscope (STM) displaying an antimicrobial-binder composition bound to fabric.

Referring now to the drawings, wherein like reference numbers refer to like elements in each of the several views, FIG. 1 shows a flowchart of one embodiment of a method for applying an antimicrobial to fabric with via antimicrobial-binder mixture. FIG. 2 shows a flow chart of one embodiment of a method of making a binder that may be utilized with the methods and fabric described herein.

An aqueous binder solution may contain one or more components that form a binder to bind antimicrobials to substrates. One such aqueous binder solution that may be used with the method is comprised of guar gum. In some embodiments, the aqueous binder solution may further comprise ammonium sulfate, urea, and/or methyl acryloid. In one embodiment of an aqueous binder solution, the solution comprises approximately 1.5% guar gum by weight. In another embodiment of an aqueous binder solution, the aqueous binder solution may comprise 1.5% guar gum and approximately 2.0% ammonium sulfate by weight. In another embodiment of an aqueous binder solution, the solution may comprise approximately 1.5% guar gum, approximately 2.0% ammonium sulfate, approximately 0.9-1.0% urea, and approximately 1.75% methyl acryloid by weight.

A binder may be prepared for use in treating fabrics according to the methods herein. To prepare such a binder approximately 102 pounds (approximately 46.3 kg) is heated to a temperature greater than 145° F. (63° C.). Approximately 3.5 lbs (1.59 kg) of guar gum is mixed with the water (20). Thereafter, the mixture is cooled to between approximately 135-145° F. (57-63° C.) (22). Approximately 37.5 lbs (17 kg) of water is added to the mixture. The water is at a temperature less than or equal to 145° F. Approximately 4.5 lbs (2.04 kg) of ammonium sulfate is mixed therewith (24). After mixing the ammonium sulfate with the mixture, approximately 2 lbs (0.91 kg) of urea is mixed therewith (26). Once the mixing of the urea is complete, 75 lbs (34 kg) of water and 4 lbs (1.81 kg) of methyl acryloid is added to create a binder (28). This binder may then be used in methods to treat fabric substrates.

To treat fabrics, an antimicrobial is mixed with the binder and water (000). The percentages of antimicrobial and binder used in this mixture are predetermined. In some embodiments, the weight percentage of antimicrobial is approximately 2% to 3%, and the weight percentage of the binder is approximately 2% to 3%.

Antimicrobials that may be used include organo silane quarternary amines capable of forming a spiked structure. Typically, these molecules are comprised of a silane group (R), a carbon chain ($C_xH_y$), and a quarternary amine ($NH_3$). The molecules are arranged such that the silane group is attached to one end of the carbon chain, while the amine is attached to the other end of the carbon chain, forming a molecular spike ($NH_3C_xH_yR$). One example of an organo silane quarternary amine that may be used is $NH_3C_{18}H_{36}R$.

The quarternary amine structure of the molecular functions as the point of the spike. When this structure comes into contact with a cellular membrane, it pierces the same. The puncturing in the membrane brings about destruction of nutrient transport systems and structural integrity, leading to cell death. Of note, the amine point does not operate by poisoning the cells it comes into contact with. Rather, the amine point physically punctures the membranes of such cells.

After the antimicrobial and binder are mixed with water, the temperature of the mixture is adjusted to allow antimicrobial and binder to disperse within the water. In a preferred embodiment, the temperature is adjusted to one that permits even dispersion of the antimicrobial and binder within the water. Although this temperature will vary, in a preferred embodiment, the temperature is between approximately 37° C. (approximately 100° F.) and approximately 44° C. (approximately 110° F.).

A fabric or substrate is chosen to receive the antimicrobial and binder mixture. Fabrics suitable for receiving the antimicrobial and binder mixture include, but are not limited to, cotton, nylon, polyester, and combinations thereof. Fabrics or substrates comprising aluminum may also be utilized in some embodiments.

In some embodiments, the fabric may undergo preparation steps prior to application of the antimicrobial and binder mixture (100). For example, some fabrics could be cleaned prior to the application. Cleaning may be helpful to remove potentially harmful ions, such as silver ions, that may exist on the fabrics. In some embodiments, cleaning occurs by a process called scouring. For dark shade textile fabrics, scouring comprises treating the fabric with chemicals such as soda ash, mild soap, or sequestrian. For light shade textile fabrics, scouring comprises treatment with peroxide. Light shade textile fabrics may also be cleaned in some embodiments by bleaching.

After the antimicrobial-binder mixture and fabric are prepared, the antimicrobial-binder mixture is applied to the fabric (200). Any method of applying a mixture to fabric may be utilized. Examples of such methods include, but are not limited to, dipping applications and spraying applications. In a preferred embodiment, the application method allows for even distribution of the antimicrobial-binder mixture to the fabric. One application that permits even distribution is dipping. In an embodiment using dipping, the fabric is submersed into the antimicrobial-binder mixture. In some embodiments, the submersion lasts for approximately one to two minutes.

After application of the antimicrobial-binder mixture to the fabric, the mixture is cured onto the fabric (300). In some embodiments, curing occurs by treating the fabric to temperatures of approximately 275-350° C., and preferably between 275-300° C. The time of curing depends on the fabric being utilized. By means of example, a fabric comprising cotton often needs longer curing times than a nylon or polyester fabric. One of skill in the art appreciates that the curing process is well known.

Upon completion of the curing process, the fabric is chemically bound to the cured binder and antimicrobial. The antimicrobial and binder are present on the fabric at approximately a 1:1 ratio by weight. The binder binds the fabric to the antimicrobial, such that the antimicrobial is oriented in a spike structure that is exposed on the outer surface of the fabric. The quarternary amine portion of the spike structure is oriented distal to the treated fabric, with the quarternary amine forming the peak of the spike, while the silane group is oriented proximate the fabric, so as to form a silane bond with the same.

Due to those chemical bonds, the antimicrobial remains fixed to the fabric. The antimicrobial does not leach, and remains intact after numerous washings. Table 1 shows exemplar results of tests in which infectious agents were introduced to treated fabrics generated pursuant to the methods described herein. In each test, the treated fabric was washed up to fifty times. After a number of washes, the treated fabric was introduced to either *staphylococcus auereus*, which causes Staph infections, or *klebsiella pneumonia*, which causes bacterial pneumonia. In each test, the infectious agent populations were decreased by more than 99% when exposed to the treated fabric for twenty four hours.

TABLE 1*

| Agent | Initial | 0 Washes | 25 Washes | 50 Washes |
| --- | --- | --- | --- | --- |
| S. auereus | $2.30 \times 10^9$ | <100 | 290 | 490 |
| K. pneumonia | $3.30 \times 10^8$ | <100 | 260 | 490 |

*values herein refer to colony forming units per milliliter (CFU/ml)

Unlike traditional treated fabrics, the treated fabrics generated pursuant to the methods described herein retain their ability to kill infectious agents after numerous washings.

Studies were also performed to determine the effectiveness of the novel treated fabrics in preventing infections. For example, Table 2 shows exemplar results of tests of the treated fabrics generated by the methods described herein. A control fabric and a treated fabric were both introduced to *clostridium difficile*, a species of harmful bacteria that is transmitted in hospitals and nursing homes. The introduced sample to each fabric had an anaerobic plate count of approximately 1,800,000.

TABLE 2*

| Fabric | Initial | 1 hour | 12 hours | 24 hours |
|---|---|---|---|---|
| Control | 1,800,000 | 2,000,000 | 1,900,000 | 1,800,000 |
| Treated |  | 230,000 | <100 | <100 |

*values herein refer to anaerobic plate counts

As seen in Table 2, after one hour, the population of the harmful *clostridium difficile* bacteria reduced by over 87% percent on the treated fabric. After twelve hours, the population of the harmful *clostridium difficile* bacteria decreased by over 99%. The bacteria population on the untreated fabric, however, remained at or above the initial population. As seen from these results, the speed at which these fabrics kill harmful infectious agents is significantly faster than that of traditionally treated fabrics, which require at least twenty four hours of contact before becoming effective at killing such agents. Additional tests demonstrated that the treated fabrics prepared according to the methods disclosed herein are effective against viruses, such as H1N1, and superbugs, such as MRCA.

Although the present methods, compositions, and fabrics have been shown and described in considerable detail with respect to only a few/particular exemplary embodiments thereof, it should be understood by those skilled in the art that it is not intended to limit the methods, compositions, or fabrics to the embodiments since various modifications, omissions, and additions may be made to the disclosed embodiments without materially departing from the novel teachings and advantages described herein, particularly in light of the foregoing teachings.

What is claimed:

1. A method of making a binder, the method comprising
    mixing guar gum with water to form a guar gum-water mixture, wherein the water is at a temperature in excess of 145° F.;
    cooling the guar gum-water mixture to approximately 135-145° F.;
    mixing ammonium sulfate and water to the guar gum-water mixture to form an ammonium sulfate-guar gum-water mixture, wherein the water is at a temperature less than or equal to 145° F.;
    mixing urea to the ammonium sulfate-guar gum-water mixture to form, a urea-ammonium sulfate-guar gum-water mixture; and
    adding water and methyl acryloid to the urea-ammonium sulfate-guar gum-water mixture to form the binder.

2. The method of claim 1, wherein mixing guar gum with water comprises mixing 46.3 kg of water with approximately 1.59 kg of guar gum.

3. The method of claim 1, wherein mixing ammonium sulfate and water to the guar gum-water mixture to form an ammonium sulfate-guar gum-water mixture comprises mixing 17 kg of water and 2.04 kg of ammonium sulfate with the guar gum-water mixture.

4. The method of claim 1, wherein mixing urea to the ammonium sulfate-guar gum-water mixture to form a urea-ammonium sulfate-guar gum-water mixture comprises mixing 0.91 kg of urea with the ammonium sulfate-guar gum-water mixture.

5. The method of claim 1, wherein adding water and methyl acryloid to the urea-ammonium sulfate-guar gum-water mixture to form the binder comprises mixing 34 kg of water and 1.81 kg of methyl acryloid with the urea-ammonium sulfate-guar gum-water mixture.

6. The method of claim 1, wherein the binder is characterized by comprising approximately 1.5% guar gum by weight, approximately 2% ammonium sulfate by weight, approximately 0.9-1.0% urea by weight, and approximately 1.75% methyl acryloid by weight.

7. A method of making a binder, the method comprising
    mixing approximately 1.59 kg guar gum with approximately 46.3 kg water to form a guar gum-water mixture, wherein the water is at a temperature in excess of 145° F.;
    cooling the guar gum-water mixture to approximately 135-145° F.;
    mixing approximately 2.04 kg ammonium sulfate and approximately 17 kg water to the guar gum-water mixture to form an ammonium sulfate-guar gum-water mixture, wherein the approximately 17 kg water is at a temperature less than or equal to 145° F.;
    mixing approximately 0.91 kg urea to the ammonium sulfate-guar gum-water mixture to form a urea-ammonium sulfate-guar gum-water mixture; and
    adding approximately 34 kg water and approximately 1.81 kg methyl acryloid to the urea-ammonium sulfate-guar gum-water mixture to form the binder.

* * * * *